US006991812B2

(12) United States Patent
Suzuki et al.

(10) Patent No.: US 6,991,812 B2
(45) Date of Patent: Jan. 31, 2006

(54) AGENT FOR PREVENTING, IMPROVING OR TREATING HYPERTENSION

(75) Inventors: Atsushi Suzuki, Tochigi (JP); Ryuji Ochiai, Tochigi (JP); Ichiro Tokimitsu, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/944,079

(22) Filed: Sep. 4, 2001

(65) Prior Publication Data

US 2002/0054923 A1 May 9, 2002

(30) Foreign Application Priority Data

| Sep. 5, 2000 | (JP) | ............................. 2000-268100 |
| Sep. 5, 2000 | (JP) | ............................. 2000-268101 |
| Sep. 5, 2000 | (JP) | ............................. 2000-268102 |
| Sep. 5, 2000 | (JP) | ............................. 2000-268103 |
| Sep. 5, 2000 | (JP) | ............................. 2000-268104 |

(51) Int. Cl.
*A61K 35/78* (2006.01)

(52) U.S. Cl. ...................................... 424/725; 562/589
(58) Field of Classification Search ................ 124/725; 514/474
See application file for complete search history.

(56) References Cited

U.S. PATENT DOCUMENTS

| 3,068,148 A | | 12/1962 | Merritt et al. |
| 4,434,177 A | * | 2/1984 | Vickers |
| 4,981,852 A | * | 1/1991 | Ahn |
| 5,883,086 A | | 3/1999 | Craft |
| 5,932,623 A | | 8/1999 | Tanabe et al. |
| 5,958,417 A | * | 9/1999 | Hsu |
| 5,994,413 A | | 11/1999 | Tanabe et al. |
| 2002/0022062 A1 | * | 2/2002 | Okawa et al. |

FOREIGN PATENT DOCUMENTS

| CA | 1128111 A | | 8/1996 |
| CA | 1185955 A | | 7/1998 |
| DE | 138406 A | | 10/1979 |
| EP | 0470895 | | 2/1992 |
| EP | 1 090 635 | | 4/2001 |
| EP | 1090635 A | | 4/2001 |
| FR | 2 302 745 | | 10/1976 |
| JP | 57058609 A | | 4/1982 |
| JP | 61194022 A | | 8/1986 |
| JP | 1203328 A | | 8/1989 |
| JP | 03258726 A | | 11/1991 |
| JP | 04243822 A | * | 8/1992 |
| JP | 6056674 A | | 3/1994 |
| JP | 7233081 | | 9/1995 |
| JP | 07 327633 A | | 12/1995 |
| JP | 8000219 A | | 1/1996 |
| JP | 8-259453 | | 10/1996 |
| JP | 9194357 A | | 7/1997 |
| JP | 9194377 A | | 7/1997 |
| JP | 10182469 A | | 7/1998 |
| JP | 10191944 | | 7/1998 |
| JP | 11263733 A | | 9/1999 |
| WO | WO 98/01143 | | 1/1998 |

OTHER PUBLICATIONS

Duffy et al. (Lancet (1999), vol. 354, pp. 2048-2049).*
R. Adams, et al., Journal of American Chemical Society, vol. 74, pps. 5346-5348, Preparation and Reactions of o-Hydroxycinnamic Acids and Esters, 1952.
Mendonca, V. L. M., et al., "Pharmacological and Toxicological Evaluation of Alpinia Speciosa," Memorias Do Instituto Oswaldo Cruz Rio De Janeiro, vol. 86, No. Suppl. 2, 1991, pp. 93-98.
Database WPI. Section Ch. Week 199241. Derwent Publications Ltd., London, GB; AN 1992-337587.
Cheng. J-T. et al. "Antihypertensive Activity of Phenolics From the Flower of Lonicera Japonica," Zhonghua Yaoxue Zazhi—Chinese Pharmaceutical Journal, Zhongguo Yaoxuehui, Taipei, TW, vol. 46, No. 6, 1994, pp. 575-582.
Maruno, Masao, "Active Principles of Pinelliae Tuber and New Preparation of Crude Drug", 1997, pp. 81-88, Abstract only.

* cited by examiner

*Primary Examiner*—Susan D. Coe
(74) *Attorney, Agent, or Firm*—Oblon, Spivak, McClelland, Maier & Neustadt, P.C.

(57) ABSTRACT

The invention relates to an agent for preventing, improving or treating hypertension, which exhibits a hypotensive effect, inhibits the rise of blood pressure and improves hypertension, and food for preventing or improving hypertension, which does not become a burden in daily intake, has a higher antihypertensive effect and is useful as a diet during treatment for patients of hypertension. The agent for preventing, improving or treating hypertension contains the following components (A) and (B):

(A) a compound selected from the group consisting of caffeic acid, chlorogenic acid and ferulic acid, and esters and pharmaceutically acceptable salts thereof; and (B) a component selected from the group consisting of central nervous system stimulating components, food fibers, extracts of perennial evergreen leaves of the genus *Camellia*, *Theaceae*, or *Eucommia ulmoides* Oliver, *Eucommiae*, organic acids having a molecular weight of 60 to 300 (excluding citric acid) and pharmaceutically acceptable salts thereof, and sugar alcohols.

20 Claims, No Drawings

AGENT FOR PREVENTING, IMPROVING OR TREATING HYPERTENSION

BACKGROUND OF THE INVENTION

1. Field of the Invention

The present invention relates to an agent for preventing, improving or treating hypertension, which permits inhibiting the rise of blood pressure and moreover improving hypertension and is useful as food and drink, and food such as food for specific health in addition to a drug for preventing, improving or treating hypertension.

2. Description of the Background Art

Cardiac diseases such as angina pectoris, myocardial infarction and heart failure, and cerebrovascular diseases such as cerebral infarction, cerebral hemorrhage and subarachnoid hemorrhage very closely relate to hypertension and stand second and third, respectively, in the Japanese causes of death. According to the basis research (the 1998 year) of the national life by the Ministry of Health and Welfare, the number of patients going to hospital regularly with hypertension is sixty-four per thousand in Japan and stands first in the cause of decease. As a countermeasure against the hypertension, may be mentioned the use of antihypertensive drugs such as diuretics, sympatholytic depressants, vasodilators and angiotensin converting enzyme inhibitors. These drugs are mainly applied to serious patients of hypertension. On the other hand, general treatments aiming at improving life custom, such as dietetic therapy, therapeutic exercise and restriction of smoking and drinking, are widely applied to slight and serious patients of hypertension. Therefore, the importance of general treatments is recognized. Among others, improvement in the custom of eating is said to be important, and there are many foods traditionally said to have a hypotensive effect. Antihypertensive materials derived from food have heretofore been extensively searched, and isolation and identification of active ingredients having a hypotensive effect have been made in large numbers. Juices of immature fruits of apple, sand pear, peach and the like, which belong to Rosaceae, contain fruit polyphenol having an inhibitory effect on an angiotensin I converting enzyme (ACE), and caffeic acid and chlorogenic acid have an ACE-inhibiting effect. It has been proposed to use such a fruit juice as an antihypertensive agent (Japanese Patent Application Laid-Open No. 259453/1996).

However, under the circumstances, many of drugs used for the purpose of treating hypertension are satisfactory in effectiveness, whereas patients are heavily burdened with their side effects, such as tachycardia and bradycardia, existing in no small numbers. With respect to foods said to have a hypotensive effect, or active ingredients thereof, the effectiveness is not always satisfactory. Further, many of them require a long time to develop a hypotensive effect.

SUMMARY OF THE INVENTION

It is an object of the present invention to provide an agent for preventing, improving or treating hypertension, which is excellent in safety, does not become a burden in daily intake and has a higher antihypertensive effect.

The present inventors have found that the combined use of a compound such as caffeic acid, chlorogenic acid or ferulic acid with a specific plant, plant extract or organic acid permits markedly inhibiting the rise of blood pressure compared with the single use of these compounds, and is suitable for use in drugs and food.

According to the present invention, there is thus provided an agent for preventing, improving or treating hypertension, comprising the following components (A) and (B):

(A) a compound selected from the group consisting of caffeic acid, chlorogenic acid and ferulic acid, and esters and pharmaceutically acceptable salts thereof; and (B) a component selected from the group consisting of central nervous system stimulating components, food fibers, extracts of perennial evergreen leaves of the genus *Camellia, Theaceae*, or *Eucommia ulmoides* Oliver, *Eucommiae*, organic acids having a molecular weight of 60 to 300 and pharmaceutically acceptable salts thereof, and sugar alcohols.

According to the present invention, there is also provided a food comprising such an agent for preventing, improving or treating hypertension.

According to the present invention, there is further provided use of the above-described components (A) and (B) for preparation of an agent for preventing, improving or treating hypertension.

According to the present invention, there is still further provided a method of treating hypertension, which comprises administering effective amounts of the components (A) and (B).

The agent for preventing, improving or treating hypertension according to the present invention exhibits a hypotensive effect, inhibits the rise of blood pressure, improves hypertension and is useful as an agent for preventing, improving or treating hypertension. Besides, the agent does not become a burden in daily intake, has a higher antihypertensive effect and is useful as a diet during treatment for patients of hypertension and also as food and drink for preventing or improving hypertension, food such as food for specific health, and a quasi-drug.

DETAILED DESCRIPTION OF THE PREFERRED EMBODIMENTS

The component (A) used in the present invention may be a product chemically synthesized. However, an extract of a natural substance containing this component, particularly, a plant may be used. Examples of the plant include coffee, onion, radish, lemon, MOROHEIYA, *Cnidium officinale* Makino, *Angelica acutiloba* Kitagawa, pine, *Captis japonica* Makino, asafetida, sugarcane, corn, barley and rice.

Caffeic acid and chlorogenic acid may also be extracted from a plant such as green beans of coffee, leaves of nandin or an immature fruit of apple. For example, an acid obtained by extraction of seeds of *Coffea arabica* LINNE, Rubiaceae with hot water or with an aqueous solution of ascorbic acid or citric acid under heating may be used.

Ferulic acid is a compound contained, as an ester thereof, in natural substances, particularly plants such as rice and adlay and may be obtained as a purified product from such a plant or a synthesized product industrially obtained. A ferulic ester is obtained in a hydrous ethanol fraction after rice bran oil obtained from rice bran is partitioned with hydrous ethanol and hexane at room temperature under weakly alkaline conditions. Ferulic acid can be obtained by hydrolyzing the ferulic ester obtained by the above-described process with sulfuric acid with heating under pressure and purifying the resultant hydrolyzate or by culturing *Pseudomonas* in a medium containing clove oil from buds and leaves of *Syzygium aromaticum* MERRILL et PERRY, Myrtaceae by steam distillation, or eugenol obtained by purifying the clove oil and subjecting the medium to isolation and purification. When ferulic acid is prepared by chemical synthesis, it may be prepared by, for example, a condensation reaction of vanillin and malonic acid (Journal of American Chemical Society, 74, 5346, 1952).

Incidentally, stereoisomers exist in caffeic acid, chlorogenic acid, ferulic acid or pharmaceutically acceptable salts thereof. However, pure stereoisomers or a mixture thereof may be used in the present invention. The term "chlorogenic acid" in the present specification means chlorogenic acid or a derivative thereof and designates 3-caffeoylquinic acid, 4-caffeoylquinic acid, 5-caffeoylquinic acid, 3,4-dicaffeoylquinic acid, 3,5-dicaffeoylquinic acid, 4,5-dicaffeoylquinic acid, 3-feruloylquinic acid, 4-feruloylquinic acid, 5-feruloylquinic acid, 3-feruloyl-4-caffeoylquinic acid or a mixture thereof.

Esters of caffeic acid, chlorogenic acid and ferulic acid include those naturally contained in natural substances, particularly, plants, those obtained by conversion by a chemical treatment upon extraction and/or fractionation and those chemically modified. Specific examples thereof include esters with an alcohol having 1 to 40 carbon atoms, i.e., ester compounds with a linear or branched alkyl or alkenyl alcohol, allyl alcohol, terpene alcohol, sterol or trimethylsterol, and esters with plant sterol. As with ferulic acid, their corresponding esters of caffeic acid and chlorogenic acid may be used.

The solubility of caffeic acid, chlorogenic acid and ferulic acid in water can be improved by providing them in the form of a pharmaceutically acceptable salt, and their physiological effectiveness can be enhanced. Examples of a basic substance used for forming such a salt include inorganic bases such as alkali metal or alkaline earth metal hydroxides, for example, such as lithium hydroxide, sodium hydroxide, potassium hydroxide, magnesium hydroxide and calcium hydroxide; and ammonium hydroxide; and organic bases, such as basic amino acids such as arginine, lysine, histidine and ornithine; and monoethanolamine, diethanolamine and triethanolamine, with the alkali metal or alkaline earth metal hydroxides being particularly preferred. The agents according to the present invention may be formulated either by preparing such a salt and adding the salt to other components, or by separately adding a salt-forming component and a component to be formed into a salt to other components to react them in the formulation system.

Two or more of the above-described compounds may be used in combination as the component (A) according to the present invention.

In the agent according to the present invention for preventing, improving or treating hypertension, the component (A) may be contained in a proportion of 0.001 to 5% by weight (hereinafter indicated merely by "%"), preferably 0.005 to 5%, more preferably 0.005 to 1%, particularly preferably 0.01 to 1%.

As the component (B) used in the present invention, the central nervous system stimulating components serve to stimulate the central nervous system to induce an exciting effect and are preferably selected from the group consisting of heat components of ginger, red pepper, pepper and the like. Ginger, red pepper and pepper are known as spice.

As ginger, red pepper and pepper, plants belonging to Zingiberaceae, *Capsicum* and Piperaceae, respectively, are used. With respect to the heat components of these plants, cinerol, zingerone, zingerol, shogaol and the like are contained in a proportion of 0.6 to 10% in ginger, capsaicin and the like are contained in a proportion of about 20% in red pepper, and piperine or the like are contained in a proportion of about 6 to 13% in pepper. These heat components may be either extracts obtained by solvent extraction making use of an organic solvent or the like, or commercially available products. Two or more of these heat components may be used in combination.

When the component (B) is a central nervous system stimulating component, it is preferably contained in a proportion of 0.001 to 1%, particularly 0.005 to 0.5% in the agent according to the present invention for preventing, improving or treating hypertension.

Specific examples of the food fibers as the component (B) used in the present invention include wheat bran composed of exodermis (testa and embryo) prepared by sieving in a milling process of wheat, beet fibers prepared by sieving after grinding of beet pulp, corn fibers prepared by purifying an exodermis division obtained from a wet milling process of corn flour, apple fibers prepared by drying pulp (residue after squeezing of juice, and the like) derived from an apple fruit, cellulose prepared by hydrolyzing pulp and then purified and drying the hydrolyzate, hardly digestible dextrin prepared by partially hydrolyzing starch, further hydrolyzing the partial hydrolyzate with amylase and then decoloring and desalting the hydrolyzate, a decomposed product of guar gum prepared by subjecting guar gum taken out of guar, which is a leguminous plant in an Indian region, to an enzymatic treatment, thyrium testa prepared by grinding testa and exodermis of a plant of Plataginaceae, alginic acid extracted from tang or low molecular sodium alginate prepared by heating and hydrolyzing alginic acid to lower the molecular weight of alginic acid, thereby enhancing the solubility thereof, chitin which is a basic polysaccharide purified by treating a crab shell or the like, or chitosan obtained by leaving the acetyl groups in chitin to make soluble in an acid solution, glucomannan purified by grinding a tuberous root of devil's-tongue to remove starch and washing the resultant devil's-tongue flour with alcohol or water, and lignin which is a phenolic high molecular compound prepared as it is from pulp, hull or bran of cacao or other plants, or from a product obtained by subjecting it to a physiochemical treatment or chemical pretreatment.

Carrageenan, agar, xanthan gum, durane gum, pullulan, pectin, methyl cellulose, which are generally used in food, may also be mentioned.

As the food fibers, are particularly preferred chitosan, lignin, hardly digestible dextrin, alginic acid and low molecular sodium alginate. Two or more of these food fibers may be used in combination.

When the component (B) is food fiber, a drink or food is preferably provided.

When the component (B) is food fiber, it is preferably contained in a proportion of 0.1 to 20%, particularly 0.5 to 10% in the agent according to the present invention for preventing, improving or treating hypertension.

Examples of the extracts of perennial evergreen leaves of the genus *Camellia*, Theaceae as the component (B) used in the present invention include parched (Chinese style) green tea and roasted (Japanese style) green tea as unfermented tea, HOSHU tea and oolong tea as semi-fermented tea, and black tea (leaf, broken, etc.) as fermented tea.

Examples of the extract of *Eucommia ulmoides* Oliver include those produced by subjecting leaves collected from *Eucommia ulmoides* Oliver, Eucommiae to solar drying and roasting.

These extracts are preferably extracts with water or an organic solvent. Examples of the organic solvent include methanol, ethanol, acetic acid, ethyl acetate, n-hexane, acetone, benzene, petroleum ether and chloroform. Extracts with ethanol or water are more preferred. The extracts may be used as it is. However, concentrates obtained by partially removing the solvent, or powders obtained by removing the solvent may be used. Two or more of these extracts may be used in combination. The extracts of *Eucommia ulmoides* Oliver and oolong tea are preferred.

A preferred combination with the component (A) includes a combination of ferulic acid and the extract of oolong tea or *Eucommia ulmoides* Oliver, and a combination of ferulic acid and the extract of oolong tea is more preferred from the viewpoint of easy drinking in view of continuous use or intake.

When the component (B) is one of these extracts, it is contained in a proportion of 0.1 to 10%, particularly 1 to 5% in terms of solids in the agent according to the present invention for preventing, improving or treating hypertension.

Examples of the organic acids having a molecular weight of 60 to 300 as the component (B) used in the present invention include carboxylic acids, hydroxycarboxylic acids, polycarboxylic acids, keto-carboxylic acids and the like from the viewpoint of structure, and specific examples thereof include acetic acid, lactic acid, citric acid, gluconic acid, fumaric acid, α-ketoglutaric acid, succinic acid, glycolic acid, malic acid, tartaric acid, pyruvic acid and malonic acid. As the organic acids, are preferred other organic acid than citric acid.

Those naturally contained in natural substances, particularly, plants, those converted by a chemical treatment upon extraction and/or fractionation and those chemically modified are also included. Examples of those derived from the natural substances include brewed vinegar prescribed in the Japanese Agricultural Standard and extracts thereof. The term "brewed vinegar" as used herein means vinegar made by acetic acid fermentation, and specific examples thereof include grain vinegar using rice or other grains as a raw material, for example, grain vinegar called "black vinegar" made by stationary brewing by a single-stage fermentation making use of brown rice and koji as raw materials, fruit vinegar making use of apple, grape or any other fruit, and other brewed vinegar than grain vinegar and fruit vinegar. Fruit juices or extracts thereof may also be used. Specific examples thereof include juices of fruits such as orange, mandarin orange, apple, grape, pineapple, peach, grapefruit, lemon, Japanese pear, pear, Japanese apricot, navel orange, strawberry, passion fruits, melon, lime, guava, apricot, SHIKUWASSHA, kabosu orange, shaddock, iyokan orange, hassaku orange, cranberry, banana, Japanese plum, mango, kiwi fruit, persimmon and ASERORA, mixed juices and concentrates thereof, and extracts thereof with water, ethanol, methanol, acetic acid, chloroform, dichloromethane, ethyl acetate, n-hexane, acetone, benzene, petroleum ether, ether or the like. Extracts with water or ethanol are particularly preferred.

Two or more of these organic acids may be used in combination.

When the component (B) is an organic acid having a molecular weight of 60 to 300, it is contained in a proportion of 0.0005 to 10%, particularly 0.001 to 6% in the agent according to the present invention for preventing, improving or treating hypertension.

Examples of the sugar alcohols as the component (B) used in the present invention include those naturally contained in natural substances, particularly, plants, those converted by a chemical treatment upon extraction and/or fractionation and those chemically modified. Specific examples of the sugar alcohols used include those obtained by reducing the carbonyl groups in monosaccharides, oligosaccharides, polysaccharides and the like to convert them to their corresponding alcohols. Specific examples of monosaccharide alcohols include erythritol which is a sugar alcohol of a tetrose, xylitol from a pentose, and sorbitol and mannitol from a hexose, which are selected by fermentationally decomposing glucose with yeast. Specific examples of oligosaccharide alcohols include parathinit (reduced parathinose), maltitol (reduced maltose) and lactitol of disaccharide sugars, and branched oligosaccharide alcohols. Specific examples of polysaccharide alcohols include reduced dextrin used as reduced starch syrup.

Among these, erythritol, xylitol, maltitol, parathinit, reduced dextrin and branched oligosaccharide alcohols are preferred.

Two or more of these sugar alcohols may be used in combination.

When the component (B) is a sugar alcohol, it is contained in a proportion of 0.1 to 70%, particularly 1 to 50% in the agent according to the present invention for preventing, improving or treating hypertension.

When the agent according to the present invention for preventing, improving or treating hypertension is used as a medicine, a pharmaceutically acceptable carrier may be added to the above-described active components to prepare an oral or parenteral composition. Forms of the oral composition include tablets, granules, grains, pills, powder, capsules (including hard capsules and soft capsules), troches, chewable preparations and solutions (drinks). On the other hand, forms of the parenteral composition include intravenously administering preparations such as injections, suppositories, and external skin care preparations.

When the agent according to the present invention for preventing, improving or treating hypertension is used as a food, other food stuffs may be added to the active ingredients of the components (A) and (B). Examples of the food include drinks and foods, and foods for specific health, such as drinks such as juice and coffee; liquid foods such as soup; emulsion or paste foods such as milk or curry; semisolid foods such as jelly or gumi; solid foods such as gum, bean curd or supplement; powdered foods; and oil-containing foods such as margarine, mayonnaise and dressing. Drinks are particularly preferred.

The effective dose of the agent according to the present invention for preventing, improving or treating hypertension per day for an adult (body weight: 60 kg) is as follows:

When the component (B) is a central nervous system stimulating component, caffeic acid, chlorogenic acid, ferulic acid or a pharmaceutically acceptable salt thereof is preferred as the component (A). The component (A) is preferably ingested in a dose of 0.001 to 10 g, particularly 0.01 to 5 g, while the central nervous system stimulating component is preferably ingested in a dose of 0.0001 to 1 g, particularly 0.001 to 0.5 g.

When the component (B) is food fiber, the component (A) is preferably ingested in a dose of 0.001 to 10 g, particularly 0.005 to 5 g, and the food fiber is preferably ingested in a dose of 0.1 to 50 g, particularly 1 to 10 g.

When the component (B) is an extract of perennial evergreen leaves of the genus Camellia, Theaceae, or *Eucommia ulmoides* Oliver, Eucommiae, the component (A) is preferably ingested in a dose of 0.001 to 10 g, particularly 0.005 to 5 g, and the extract is preferably ingested in a dose of 0.01 to 50 g, particularly 0.05 to 10 g in terms of solids.

When the component (B) is an organic acid having a molecular weight of 60 to 300 or a pharmaceutically acceptable salt thereof, the component (A) is preferably ingested in a dose of 0.0001 to 5 g, particularly 0.0005 to 1 g in terms of ferulic acid, and the organic acid or the like is preferably ingested in a dose of 0.0001 to 5 g, particularly 0.0005 to 1 g in terms of citric acid.

When the component (B) is a sugar alcohol, the component (A) is preferably ingested in a dose of 0.001 to 10 g, particularly 0.005 to 5 g, and the sugar alcohol is preferably ingested in a dose of 0.1 to 50 g, particularly 1 to 20 g.

EXAMPLE

Testing Method of Inhibiting the Rise of Blood Pressure in Rat (a) Animal Used:

The blood pressure of each of male spontaneous hypertensive rats (SHR) was preliminarily continuously measured for 7 days by means of a commercially available non-invasive sphygmomanometer (manufactured by Softlon Co.), thereby fully accustoming the rats to the sphygmomanometry, and an evaluation test was then started. All the rats were bred (in a breeding chamber in a rat zone) under conditions of a temperature of 25±1° C., a relative humidity of 55±10% and a lighting time of 12 hours (from 7 a.m. to 7 p.m.).

(b) Testing Method:

Six or eight SHRs were used as a group. The systolic blood pressure of a tail artery of each rat was measured after 4 weeks from the beginning of the test.

(c) Statistical Processing Method:

The thus-obtained test results were expressed by a mean and standard error to conduct a Student's t-test. A level of significance was defined as at most 5%.

Example 1

Central Nervous System Stimulating Component

In Control Group, drinking water and a commercially available powdered feed were freely ingested. In Comparative Group 1, a solution with ferulic acid (product of Wako Pure Chemical Industries, Ltd.) added to water at a concentration of 0.2% was used as drinking water, and a commercially available powdered feed was freely ingested. In Test Group 1, a solution with caffeic acid (product of Wako Pure Chemical Industries, Ltd.) added to water at a concentration of 0.2% was used as drinking water, and a feed with capsaicin (product of Wako Pure Chemical Industries, Ltd.; 0.1%) incorporated into a commercially available powdered feed was freely ingested. In Test Group 2, a solution with chlorogenic acid (product of Wako Pure Chemical Industries, Ltd.) added to water at a concentration of 0.2% was used as drinking water, and a feed with zingerol (product of Matsuura Yakugyo K.K.; 0.1%) incorporated into a commercially available powdered feed was freely ingested. In Test Group 3, a solution with ferulic acid added to water at a concentration of 0.2% was used as drinking water, and a feed with piperine (product of Wako Pure Chemical Industries, Ltd.; 0.1%) incorporated into a commercially available powdered feed was freely ingested. In each group, 6 rats aged 7 weeks at the time the intake test was started were used.

The systolic blood pressures in each group before the administration and after 4 weeks from the administration are shown in Table 1. As apparent from Table 1, a marked inhibitory effect on the rise of blood pressure was observed by using caffeic acid, chlorogenic acid, ferulic acid or the pharmaceutically acceptable salt thereof and the Central nervous system stimulating component in combination.

TABLE 1

| | Systolic blood pressures (mmHg) | |
|---|---|---|
| | Before administration | After 4 weeks from administration |
| Control Group | 146.2 ± 4.2 | 201.0 ± 4.9 |
| Comp. Group 1 | 148.8 ± 3.8 | 190.7 ± 3.4 |
| Test Group 1 | 146.8 ± 4.8 | 181.5 ± 3.4 * |
| Test Group 2 | 144.1 ± 3.5 | 180.3 ± 3.6 * |
| Test Group 3 | 145.6 ± 4.5 | 178.7 ± 4.1 * |

*: There is a significant difference at a significance level of at most 5% as against Control Group and Comparative Group 1.
Each value is expressed by mean ± standard error.

Example 2

Central Nervous System Stimulating Component (Immediate Effect)

Six rats aged 15 weeks at the time the administration test was started were used in each group. The systolic blood pressure of a tail artery of each rat was measured after 1 hour from the beginning of the administration.

In Control Group, water was orally administered. In Comparative Group 1, a 0.2% aqueous solution of ferulic acid was orally administered. In Test Group 1, an aqueous solution containing caffeic acid (0.2%) and capsaicin (0.1%) was orally administered. In Test Group 2, an aqueous solution containing chlorogenic acid (0.2%) and zingerol (0.1%) was orally administered. In Test Group 3, an aqueous solution containing ferulic acid (0.2%) and piperine (0.1%) was orally administered.

The systolic blood pressures in each group before the administration and after 1 hour from the administration are shown in Table 2. As apparent from Table 2, marked lowering of blood pressure was observed.

TABLE 2

| | Systolic blood pressures (mmHg) | |
|---|---|---|
| | Before administration | After 1 hour from administration |
| Control Group | 209.6 ± 4.3 | 206.2 ± 4.4 |
| Comp. Group 1 | 206.1 ± 2.6 | 196.4 ± 3.9 |
| Test Group 1 | 208.5 ± 3.4 | 178.1 ± 5.8 * |
| Test Group 2 | 207.1 ± 3.0 | 180.3 ± 5.2 * |
| Test Group 3 | 208.9 ± 4.5 | 179.5 ± 4.6 * |

*: There is a significant difference at a significance level of at most 5% as against Control Group and Comparative Group 1.
Each value is expressed by mean ± standard error.

Example 3

Food Fiber

In Control Group, drinking water and a commercially available powdered feed were freely ingested. In Test Group 1, a feed with chitosan (5%) incorporated into a commercially available powdered feed was freely ingested. In Test Group 2, a solution with caffeic acid added to water at a concentration of 0.2% was used as drinking water, and a feed with chitosan (5%) incorporated into a commercially available powdered feed was freely ingested. In Test Group 3, a solution with chlorogenic acid added to water at a concentration of 0.2% was used as drinking water, and a feed with chitosan (5%) incorporated into a commercially available powdered feed was freely ingested. In Test Group 4, a solution with ferulic acid added to water at a concentration of 0.2% was used as drinking water, and a feed with chitosan (5%) incorporated into a commercially available powdered feed was freely ingested. In Test Group 5, a solution with sodium ferulate added to water at a concentration of 0.2% was used as drinking water, and a feed with chitosan (5%) incorporated into a commercially available powdered feed was freely ingested. In Test Group 6, a solution with cycloartenol ferulate added to water at a concentration of 0.2% was used as drinking water, and a feed with chitosan (5%) incorporated into a commercially available powdered feed was freely ingested. In each group, 6 rats aged 7 weeks at the time the intake test was started were used.

The systolic blood pressures in each group before the administration and after 4 weeks from the administration are shown in Table 3. As apparent from Table 3, marked lowering of blood pressure was observed by using caffeic acid, chlorogenic acid, ferulic acid, or the ester or pharmaceutically acceptable salt thereof and the food fiber in combination as compared with the single administration of the food fiber.

TABLE 3

| | Systolic blood pressures (mmHg) | |
|---|---|---|
| | Before administration | After 4 weeks from administration |
| Control Group | 152.1 ± 4.4 | 201.0 ± 3.9 |
| Test Group 1 | 153.4 ± 2.9 | 186.7 ± 4.5 * |
| Test Group 2 | 154.0 ± 4.3 | 173.5 ± 4.3 **# |
| Test Group 3 | 155.1 ± 3.9 | 170.6 ± 4.2 **# |
| Test Group 4 | 153.7 ± 4.8 | 169.7 ± 5.0 **# |
| Test Group 5 | 155.7 ± 3.2 | 172.9 ± 4.6 **# |
| Test Group 6 | 152.9 ± 3.0 | 168.1 ± 4.7 **# |

*, **: There are significant differences at significance levels of at most 5% and 1% as against Control Group, respectively.
: There is a significant difference at a significance level of at most 5% as against Test Group 1.
Each value is expressed by mean ± standard error.

Example 4

Extract of Perennial Evergreen Leaves of the Genus *Camellia*, Theaceae

In Control Group, drinking water and a commercially available powdered feed were freely ingested. In Test Group 1, a solution with ferulic acid (product of Wako Pure Chemical Industries, Ltd.) dissolved in drinking water at a concentration of 0.2% was freely ingested. In Test Group 2, drinking water and a feed with powdered green tea extract ("Ryokucha Shokubutsu MF", trade name, product of Maruzen Seiyaku K.K.; 3%) incorporated into a commercially available powdered feed were freely ingested. In Test Group 3, a solution with ferulic acid added to water at a concentration of 0.2% was used as drinking water, and a feed with the powdered green tea extract (3%) incorporated into a commercially available powdered feed was freely ingested. In Test Group 4, a solution with chlorogenic acid (product of Wako Pure Chemical Industries, Ltd.) added to water at a concentration of 0.2% was used as drinking water, and a feed with powdered oolong tea extract ("Sunoolong", trade name, product of Suntory Limited; 3%) incorporated into a commercially available powdered feed was freely ingested. In each group, 6 rats aged 16 weeks at the time the intake test was started were used.

The systolic blood pressures in each group before the administration and after 4 weeks from the administration are shown in Table 4. As apparent from Table 4, the compositions according to the present invention for eating and drinking were observed having a marked effect to lower blood pressure.

TABLE 4

| | Systolic blood pressures (mmHg) | |
|---|---|---|
| | Before administration | After 4 weeks from administration |
| Control Group | 146.2 ± 4.2 | 201.0 ± 4.9 |
| Test Group 1 | 144.1 ± 2.8 | 190.4 ± 3.3 * |
| Test Group 2 | 145.0 ± 4.4 | 191.8 ± 3.9 * |
| Test Group 3 | 144.7 ± 4.0 | 180.3 ± 2.2 *# |
| Test Group 4 | 145.1 ± 5.3 | 179.2 ± 2.7 *# |

*: There is a significant difference at a significance level of at most 5% as against Control Group.
: There is a significant difference at a significance level of at most 5% as against Test Groups 1 and 2.
Each value is expressed by mean ± standard error.

Example 5

Extract of *Eucommia ulmoides* Oliver

Evaluation as to lowering of blood pressure was made in the same manner as in Example 4.

In Control Group, drinking water and a commercially available powdered feed were freely ingested. In Test Group 1, drinking water and a feed with powdered extract of tea leaves of *Eucommia ulmoides* Oliver ("Tochucha Ekisu", trade name, product of Matsuura Seiyaku K.K.; 3%) incorporated into a commercially available powdered feed were freely ingested. In Test Group 2, a solution with ferulic acid added to water at a concentration of 0.2% was used as drinking water, and a feed with the powdered extract (3%) of tea leaves of *Eucommia ulmoides* Oliver incorporated into a commercially available powdered feed was freely ingested. In Test Group 3, drinking water and a feed with powdered triterpenyl ferulate mixture (1%) derived from rice bran and the powdered extract (3%) of tea leaves of *Eucommia ulmoides* Oliver incorporated into a commercially available powdered feed were freely ingested.

The systolic blood pressures in each group before the administration and after 4 weeks from the administration are shown in Table 5. As apparent from Table 5, marked lowering of blood pressure was observed by ingesting the compositions according to the present invention for eating and drinking.

TABLE 5

| | Systolic blood pressures (mmHg) | |
|---|---|---|
| | Before administration | After 4 weeks from administration |
| Control Group | 146.2 ± 4.2 | 201.0 ± 4.9 |
| Test Group 1 | 144.3 ± 3.8 | 188.6 ± 4.2 * |

TABLE 5-continued

| | Systolic blood pressures (mmHg) | |
|---|---|---|
| | Before administration | After 4 weeks from administration |
| Test Group 2 | 146.0 ± 3.9 | 174.3 ± 3.1 *# |
| Test Group 3 | 145.1 ± 4.6 | 172.8 ± 4.0 *# |

*: There is a significant difference at a significance level of at most 5% as against Control Group.
: There is a significant difference at a significance level of at most 5% as against Test Group 1.
Each value is expressed by mean ± standard error.

Example 6

Organic Acid Immediate Effect

Six rats aged 15 weeks at the time the administration test was started were used in each group. The systolic blood pressure of a tail artery of each rat was measured after 1 hour from the beginning of oral administration.

In Control Group, drinking water was orally administered forcedly by means of a metal-made stomach tube. In Comparative Group 1, a 0.1% aqueous solution of malic acid was orally administered. In Comparative Group 2, a 0.1 aqueous solution of ferulic acid was orally administered. In Test Group 1, an aqueous solution containing malic acid (0.1%) and ferulic acid (0.1%) was orally administered.

The systolic blood pressures in each group before the administration and after 1 hour from the administration are shown in Table 6. As apparent from Table 6, marked lowering of blood pressure was observed by administering the composition according to the present invention.

TABLE 6

| | Systolic blood pressures (mmHg) | |
|---|---|---|
| | Before administration | After 1 hour from administration |
| Control Group | 206.8 ± 3.4 | 198.0 ± 5.6 |
| Comp. Group 1 | 206.1 ± 2.6 | 196.4 ± 3.9 * |
| Comp. Group 2 | 208.0 ± 4.1 | 179.7 ± 4.4 *# |
| Test Group 1 | 207.4 ± 3.3 | 170.6 ± 2.1 ***# |

*, ***: There are significant differences at significance levels of at most 5% and 0.1% as against Control Group, respectively.
: There is a significant difference at a significance level of at most 5% as against Comparative Group 2.
Each value is expressed by mean ± standard error.

Example 7

Sugar Alcohol

In Control Group, a 1% aqueous solution of sugar was used as drinking water, and a commercially available solid feed was freely ingested. In Test Group 1, an aqueous solution containing ferulic acid (product of Wako Pure Chemical Industries, Ltd.; 0.1%) and sugar (1%) was used as drinking water, and a commercially available solid feed was freely ingested. In Test Group 2 (Invention), an aqueous solution containing ferulic acid (0.1%) and erythritol (product of Wako Pure Chemical Industries, Ltd.; 1%) was used as drinking water, and a commercially available solid feed was freely ingested. In each group, 8 rats aged 8 weeks at the time the intake test was started were used.

The systolic blood pressures in each group before the administration and after 4 weeks from the administration are shown in Table 7. As apparent from Table 7, a marked inhibitory effect on the rise of blood pressure was observed by ingesting the invention composition in Test Group 2.

TABLE 7

| | Systolic blood pressures (mmHg) | |
|---|---|---|
| | Before administration | After 4 weeks from administration |
| Control Group | 148.1 ± 3.2 | 195.0 ± 4.3 |
| Test Group 1 | 148.3 ± 3.6 | 187.1 ± 3.2 |
| Test Group 2 | 148.5 ± 4.1 | 180.7 ± 3.8 * |

*: There is a significant difference at a significance level of at most 5% as against Control Group.
Each value is expressed by mean ± standard error.

Example 8

Sugar Alcohol Immediate Effect

Six rats aged 15 weeks at the time the administration test was started were used in each group. The systolic blood pressure of a tail artery of each rat was measured after 1 hour from the beginning of oral administration.

In Control Group, a 1% aqueous solution of sugar was orally administered. In Test Group 1, an aqueous solution containing ferulic acid (0.2%) and sugar (1%) was orally administered. In Test Group 2, an aqueous solution containing ferulic acid (0.2%) and erythritol (1%) was orally administered. The dose was determined to be 15 mL/kg.

The systolic blood pressures in each group before the administration and after 1 hour from the administration are shown in Table 8. As apparent from Table 8, marked lowering of blood pressure was observed by administering the composition according to the present invention.

TABLE 8

| | Systolic blood pressures (mmHg) | |
|---|---|---|
| | Before administration | After 1 hour from administration |
| Control Group | 206.8 ± 3.4 | 207.2 ± 3.2 |
| Test Group 1 | 208.0 ± 3.5 | 184.6 ± 3.4 ** |
| Test Group 2 | 208.3 ± 4.6 | 175.7 ± 2.4 **# |

*, **: There are significant differences at significance levels of at most 5% and 1% as against Control Group, respectively.
: There is a significant difference at a significance level of at most 5% as against Test Group 1.
Each value is expressed by mean ± standard error.

Example 9

Soft Capsule Preparation

| Composition of soft capsule: | |
|---|---|
| Gelatin | 70.0% |
| Glycerol | 22.9 |
| Methyl p-hydroxybenzoate | 0.15 |
| Propyl p-hydroxybenzoate | 0.51 |
| Water | 6.44 |

The soft capsule (oval form, weight: 150 mg) composed of the above composition was charged with the following components to prepare a soft capsule preparation.

TABLE 9

| | (mg) | | |
|---|---|---|---|
| No. | 1 | 2 | 3 |
| Ferulic acid | 50 | 50 | 50 |
| capsaicin | 100 | | |
| Powdered green tea extract | | 450 | |
| Maltitol | | | 450 |

All the soft capsule preparations Nos. 1 to 3 exhibited a good effect to lower blood pressure.

Example 10

Cookie

Cookies composed of their corresponding compositions shown in Table 10 were baked.

TABLE 10

| No. | 4 | 5 | 6 | 7 | 8 |
|---|---|---|---|---|---|
| | (g) | | | | |
| Ferulic acid | 1 | | | | |
| Cycloartenol ferulate [1]) | | | 1 | 1 | 1 |
| Extract of coffee bean | | 1 | | | |
| Piperine | 1 | | | | |
| Lignin | | 15 | | | |
| Powdered extract of oolong tea | | | 5 | | |
| Orange extract | | | | 5 | 5 |
| Reduced dextrin | | | | | 14 |
| Cacao extract | | 5 | | | |
| Rapeseed oil | 15 | | 10 | 15 | 12 |
| Soybean oil | | 15 | | | |
| Corn starch | 15 | | 15 | 15 | 12 |
| Wheat | 50 | 44 | 46 | 50 | 40 |
| Butter | 5 | 5 | 5 | 5 | 5 |
| Fructose | 14 | 14 | 14 | 14 | |
| Common salt | 0.5 | 0.5 | | 0.5 | 0.5 |
| Baking soda | 0.5 | 0.5 | | 0.5 | 0.5 |
| Water | 10 | 10 | | 10 | 10 |

[1]) Product of Wako Pure Chemical Industries, Ltd.

These cookies Nos. 4 to 8 were tasty and observed permitting being ingested by adults suffering from hypertension.

Example 11

Healthy Drink

Healthy drinks composed of their corresponding compositions shown in Table 11 were prepared.

TABLE 11

| No. | 9 | 10 | 11 | 12 | 13 | 14 |
|---|---|---|---|---|---|---|
| | (%) | | | | | |
| Sodium ferulate | 3.5 | | | | | |
| Ginger extract | 0.1 | 0.1 | 0.1 | 0.1 | 0.1 | |
| Lactic acid | 0.1 | 0.1 | 0.1 | 0.1 | 0.1 | 0.1 |
| Malic acid | | | | | | 0.1 |
| Alginic acid | | 3.5 | | | | |

TABLE 11-continued

| No. | 9 | 10 | 11 | 12 | 13 | 14 |
|---|---|---|---|---|---|---|
| Powdered extract of tea leaves of *Eucommia ulmoides* Oliver | | 5.0 | | | | |
| Lemon extract | | | | 3.5 | 3.5 | 3.5 |
| Parathinit | | | | | 9.0 | |
| Nonfat milk | 3.5 | 3.5 | 3.5 | 3.5 | 3.5 | 3.5 |
| Fructose | 9.0 | 9.0 | 9.0 | 9.0 | | 9.0 |
| Ascorbic acid | 0.1 | 0.1 | 0.1 | 0.1 | 0.1 | 0.1 |
| Perfume base | 0.1 | 0.1 | 0.1 | 0.1 | 0.1 | 0.1 |
| water | 83.6 | 83.6 | 82.1 | 83.6 | 83.6 | 83.6 |

All the healthy drinks Nos. 9 to 14 were high in shelf stability, good in flavor and tasty.

Four adult men (the highest blood pressure: 135 mmHg) who were somewhat high in blood pressure were got to drink the healthy drink No. 10 (200 ml) every day for 4 weeks. As a result, lowering of the blood pressure by 7 mmHg was observed.

Example 12

Separate Type Dressing

| Olive oil | 40.0% |
|---|---|
| Wine vinegar | 50.0 |
| Common salt | 1.25 |
| Pepper | 0.3 |
| Sodium caffeate | 0.1 |
| Granular mustard | 8.35 |

A separate type dressing composed of the above composition was prepared.

What is claimed is:

1. A method for treating hypertension comprising:
   administering a composition consisting essentially of:
   (A) an isolated chlorogenic acid, or an ester or salt of an isolated chlorogenic acid; and
   (B) an organic acid having a molecular weight ranging from 60 to 300 or a pharmaceutically acceptable salt thereof,
   wherein said organic acid is lactic acid.

2. The method of claim 1, wherein (A) is a chlorogenic acid.

3. The method of claim 1, wherein (A) is an ester of a chlorogenic acid.

4. The method of claim 1, wherein (A) is a salt of a chlorogenic acid.

5. The method of claim 1, wherein said isolated chlorogenic acid is a pure stereoisomer.

6. The method of claim 1, wherein said isolated chlorogenic acid is a mixture of stereoisomers.

7. The method of claim 1, wherein said isolated chlorogenic acid is 4-caffeoylquinic acid.

8. The method of claim 1, wherein said isolated chlorogenic acid is 5-caffeoylquinic acid.

9. The method of claim 1, wherein said isolated chlorogenic acid is 3,4-dicaffeoylquinic acid.

10. The method of claim 1, wherein said isolated chlorogenic acid is 3,5-dicaffeoylquinic acid.

11. The method of claim 1, wherein said isolated chlorogenic acid is 4,5 dicaffeoylquinic acid.

12. The method of claim 1, wherein said isolated chlorogenic acid is 3-feruloylquinic acid.

13. The method of claim 1, wherein said isolated chlorogenic acid is 4-feruloylquinic acid.

14. The method of claim 1, wherein said isolated chlorogenic acid is 5-feruloylquinic acid.

15. The method of claim 1, wherein said isolated chlorogenic acid is 3-feruloyl-4-caffeoylquinic acid.

16. The method of claim 1, wherein said composition is in the form of a tablet, granule, grain, pill, powder, capsule, or troche.

17. The method of claim 1, comprising administering a composition consisting essentially of:
   (A) 0.001 to 5 wt. % of an isolated chlorogenic acid, or an ester or salt of an isolated chlorogenic acid; and
   (B) 0.0005 to 10 wt. % of an organic acid having a molecular weight ranging from 60 to 300 or a pharmaceutically acceptable salt thereof, wherein said organic acid is lactic acid.

18. The method of claim 1, comprising administering a composition consisting essentially of:
   (A) 0.01 to 1 wt. % of an isolated chlorogenic acid, or an ester or salt of an isolated chlorogenic acid; and
   (B) 0.001 to 6 wt. % of an organic acid having a molecular weight ranging from 60 to 300 or a pharmaceutically acceptable salt thereof, wherein said organic acid is lactic acid.

19. A method for treating hypertension comprising:
administering a composition consisting essentially of:
   (A) an isolated chlorogenic acid, or an ester or salt of an isolated chlorogenic acid;
   (B) an organic acid having a molecular weight ranging from 60 to 300 or a pharmaceutically acceptable salt thereof, wherein said organic acid is lactic acid; and
   (C) one or more solid food stuffs.

20. A method for treating hypertension comprising:
administering a composition consisting essentially of:
   (A) an isolated chlorogenic acid, or an ester or salt of an isolated chlorogenic acid;
   (B) an organic acid having a molecular weight ranging from 60 to 300 or a pharmaceutically acceptable salt thereof, wherein said organic acid is lactic acid; and
   (C) one or more liquid food stuffs.

* * * * *